(12) United States Patent
Nakaya

(10) Patent No.: US 7,563,230 B2
(45) Date of Patent: Jul. 21, 2009

(54) ULTRASOUND DIAGNOSIS APPARATUS

(75) Inventor: Shigemitsu Nakaya, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 591 days.

(21) Appl. No.: 11/020,299

(22) Filed: Dec. 27, 2004

(65) Prior Publication Data

US 2005/0187475 A1    Aug. 25, 2005

(30) Foreign Application Priority Data

Dec. 25, 2003   (JP)   ............... 2003-429740

(51) Int. Cl.
*A61B 8/14*   (2006.01)
*A61B 8/00*   (2006.01)

(52) U.S. Cl. ...................... 600/458; 600/443

(58) Field of Classification Search .......... 600/437, 600/458

See application file for complete search history.

(56) References Cited

U.S. PATENT DOCUMENTS 6,110,120  A  *  8/2000  Holley et al. ............. 600/458

6,436,049  B1  *  8/2002  Kamiyama et al. ............ 600/458

FOREIGN PATENT DOCUMENTS

| JP | 08-107895 | 4/1996 |
|---|---|---|
| JP | 08-252253 | 10/1996 |
| JP | 2003-153900 | 5/2003 |

\* cited by examiner

*Primary Examiner*—Eric F Winakur
*Assistant Examiner*—Michael T Rozanski
(74) *Attorney, Agent, or Firm*—Oblon, Spivak, McClelland, Maier & Neustadt, P.C.

(57) ABSTRACT

An ultrasound diagnosis apparatus includes a transceiver, a processor, a memory, and a display unit. The transceiver is configured to transmit an ultrasound signal to a part of a specimen and receive an echo signal resulting from the ultrasound signal transmission. The part is administered with a contrast agent. The processor is configured to prepare a moving image data based on the received echo signal. The memory is configured to store the prepared moving image data as a past moving image data. The display unit is configured to display the past moving image data and a current moving image data prepared by the processor in parallel. The past moving image data is displayed in response to an administration initiation of the contrast agent for the current moving image data.

39 Claims, 9 Drawing Sheets

42

ID:123456
Name:TOSHIBA

| Name | Date |
|------|------|
| INJ-1 | 2003-07-11 13:30 |
| INJ-2 | 2003-07-13 14:35 |
| INJ-3 | 2003-07-14 15:03 |

FIG. 6

ULTRASOUND DIAGNOSIS APPARATUS

CROSS-REFERENCE TO RELATED APPLICATION

This application is based upon and claims the benefit of priority from prior Japanese Patent Application No. P2003-429740, filed on Dec. 25, 2003, the entire contents of which are incorporated herein by reference.

BACKGROUND OF THE INVENTION

1. Field of the Invention

The present invention relates to an ultrasound diagnosis apparatus which displays an enhanced ultrasound image. The present invention also relates to a method of displaying an enhanced ultrasound image.

2. Discussion of the Background

An ultrasound diagnosis apparatus is known to be advantageous since it can allow to easily displaying, for example, a heartbeat motion or a fetus motion in real time by only applying an ultrasound probe to a body surface of a patient. Also, there is no worry about an X-ray exposure in ultrasound imaging, and thus it is safe for the patient and can be repeated without a risk of the X-ray exposure. Further, an ultrasound diagnosis apparatus can be made compact in size, compared to an X-ray diagnosis apparatus, an X-ray computed tomography (CT) apparatus, a nuclear magnetic resonance imaging apparatus, and the like. Therefore, it is easy to conduct an ultrasound imaging examination at bedside. Although the size of the ultrasound diagnosis apparatus may depend on features equipped in the apparatus, it is nowadays reduced down to a size allowing a user to bring the apparatus one-handed.

As a typical focal medical treatment of the hepatocellular carcinoma, the percutaneous ethanol injection therapy (PEIT), the percutaneous microwave coagulation therapy (PMCT), and the radiofrequency abration (RFA) may often be conducted. For example, in the percutaneous ethanol injection therapy, a paracentesis needle is penetrated towards a tumor under an ultrasound imaging guide. A medical agent is administered to the tumor through the paracentesis needle so as to extinct cancer cells. In the percutaneous microwave coagulation therapy, microwaves are exposed to the tumor and coagulate the tumor so as to extinct cancer cells. In the radio frequency abration, the tumor is heated by the high temperature so as to extinct cancer cells. It is usually quite easy to conduct any of the above medical treatment. In addition, the patient may not suffer a lot from the medical treatment.

Whether the medical treatment has successfully been conducted or not is often ascertained by imaging the patient with a dynamic CT apparatus, the nuclear magnetic resonance imaging apparatus, or the like. These medical imaging apparatuses may also be used to find where the tumor is located before the medical treatment. However, an ultrasound diagnosis apparatus is also used nowadays to ascertain or find the same since the ultrasound diagnosis apparatus has been improved recently and an intravenous contrast agent has been introduced for the ultrasound imaging. In such an enhanced ultrasound imaging technique, for example, blood flow signals may be enhanced and a dynamic state of the blood flow may be evaluated in a cardiac examination or an abdominal organ examination by administering a contrast agent from the vein, as described in Japanese Patent Application Publication No. 2003-153900.

When the enhanced ultrasound imaging technique is used to ascertain whether the medical treatment has successfully been conducted or not, images showing a specific part (typically a part of the tumor) obtained before the medical treatment are usually compared to images showing the same obtained after the medical treatment. For example, when the blood is flowing into the part of the tumor through the blood vessel before the medical treatment, the medical treatment is determined to have successfully been conducted if the blood stops flowing into the part of the tumor through the blood vessel after the medical treatment. If the blood is still flowing into the part of the tumor through the blood vessel after the medical treatment, the medical treatment is determined to have failed and required again.

In the enhanced ultrasound imaging technique, it is important to know a time phase of the ultrasound image data in the process from the administration of the contrast agent. In the case of liver, for example, the contrast agent flows into the hepar artery, the portal vein, and the like. As a result, the blood vessels are enhanced in ultrasound images displayed in a display unit. Such images in which the blood vessels are enhanced may be called vascular images. As time passes, the contrast agent continues to flow into blood capillaries and tissues inside the liver. Accordingly, the liver is enhanced as a whole in ultrasound images displayed in the display unit. Such images in which the blood capillaries and tissues (or the organ like the liver) are enhanced may be called perfusion images.

As described above, images to be displayed changes from the vascular images to the perfusion images according to the time phases in the process from the administration of the contrast agent. Therefore, time phase information and corresponding images are important as diagnosis information. For this reason, the ultrasound diagnosis apparatus capable of the enhanced ultrasound imaging technique often includes an injection timer which measures time elapsed from the administration of the contrast agent. Also as described, it is usually necessary to obtain ultrasound images (or moving images) of before and after the medical treatment in order to ascertain whether the medical treatment has successfully been conducted or not.

In conducting the enhanced ultrasound imaging technique, it maybe necessary to activate the injection timer and also to initiate storage of ultrasound images at the same time as the administration of the contrast agent. Further, after the medical treatment, it may also be necessary to retrieve appropriate enhanced images obtained before the medical treatment from an image file storing ultrasound images. Finally, it may be necessary to display and compare the ultrasound images obtained before and after the medical treatment in accordance with the time phase in the process from the administration of the contrast agent in order to ascertain whether the medical treatment has successfully been conducted or not. Consequently, a user of the ultrasound diagnosis apparatus may be required cumbersome operations from the imaging to the ascertainment.

SUMMARY OF THE INVENTION

According to the first aspect of the present invention, there is provided an ultrasound diagnosis apparatus including a transceiver, a processor, a memory, and a display unit. The transceiver is configured to transmit an ultrasound signal to a part of a specimen and receive an echo signal resulting from the ultrasound signal transmission. The part is administered with a contrast agent. The processor is configured to prepare a moving image data based on the received echo signal. The memory is configured to store the prepared moving image data as a past moving image data. The display unit is configured to display the past moving image data and a current moving image data prepared by the processor in parallel. The past moving image data is displayed in response to an administration initiation of the contrast agent for the current moving image data.

According to the second aspect of the present invention, there is provided an ultrasound diagnosis apparatus including a transceiver, a processor, a memory, and a display unit. The transceiver is configured to transmit an ultrasound signal to a part of a specimen and receive an echo signal resulting from the ultrasound signal transmission. The part is administered with a contrast agent. The processor is configured to prepare an image data based on the received echo signal. The memory is configured to store the image data for at least one image as a past image data. The display unit is configured to display the past image data and a current image data prepared by the processor in parallel. The past image data is displayed in accordance with a time phase of the current image data from an administration initiation of the contrast agent for the current image data.

According to the third aspect of the present invention, there is provided a method of displaying an ultrasound image resulting from an ultrasound diagnosis apparatus. The method begins by transmitting a first ultrasound signal to a part of a specimen and receiving a first echo signal resulting from the first ultrasound signal transmission. The part is administered with a first contrast agent. The method continues by preparing a first moving image data based on the received first echo signal and storing the prepared first moving image data as a past moving image data. The method further continues by transmitting a second ultrasound signal to the part of the specimen and receiving a second echo signal resulting from the second ultrasound signal transmission, the part being injected with a second contrast agent, preparing a second moving image data based on the received second echo signal, and displaying the past moving image data and the second moving image data in parallel as the ultrasound image. The past moving image data is displayed in response to an administration initiation of the contrast agent for the current moving image data.

BRIEF DESCRIPTION OF THE DRAWINGS

A more complete appreciation of embodiments of the present invention and many of its attendant advantages will be readily obtained by reference to the following detailed description considered in connection with the accompanying drawings, in which:

FIG. 6 is an illustration showing an example of a list of image names of pre-treatment image data;

DESCRIPTION OF THE PREFERRED EMBODIMENTS

Embodiments of the present invention will be described with reference to the accompanying drawings.

Displays according to the enhanced ultrasound imaging technique can be applied to ascertain whether the medical treatment has successfully been conducted or not on any region of interest inside the body of a specimen such as, for example, a patient. The following description, however, will be described with an example of the ascertainment by displaying an enhanced blood flow into the liver parenchyma as the region of interest.

Figure 1:
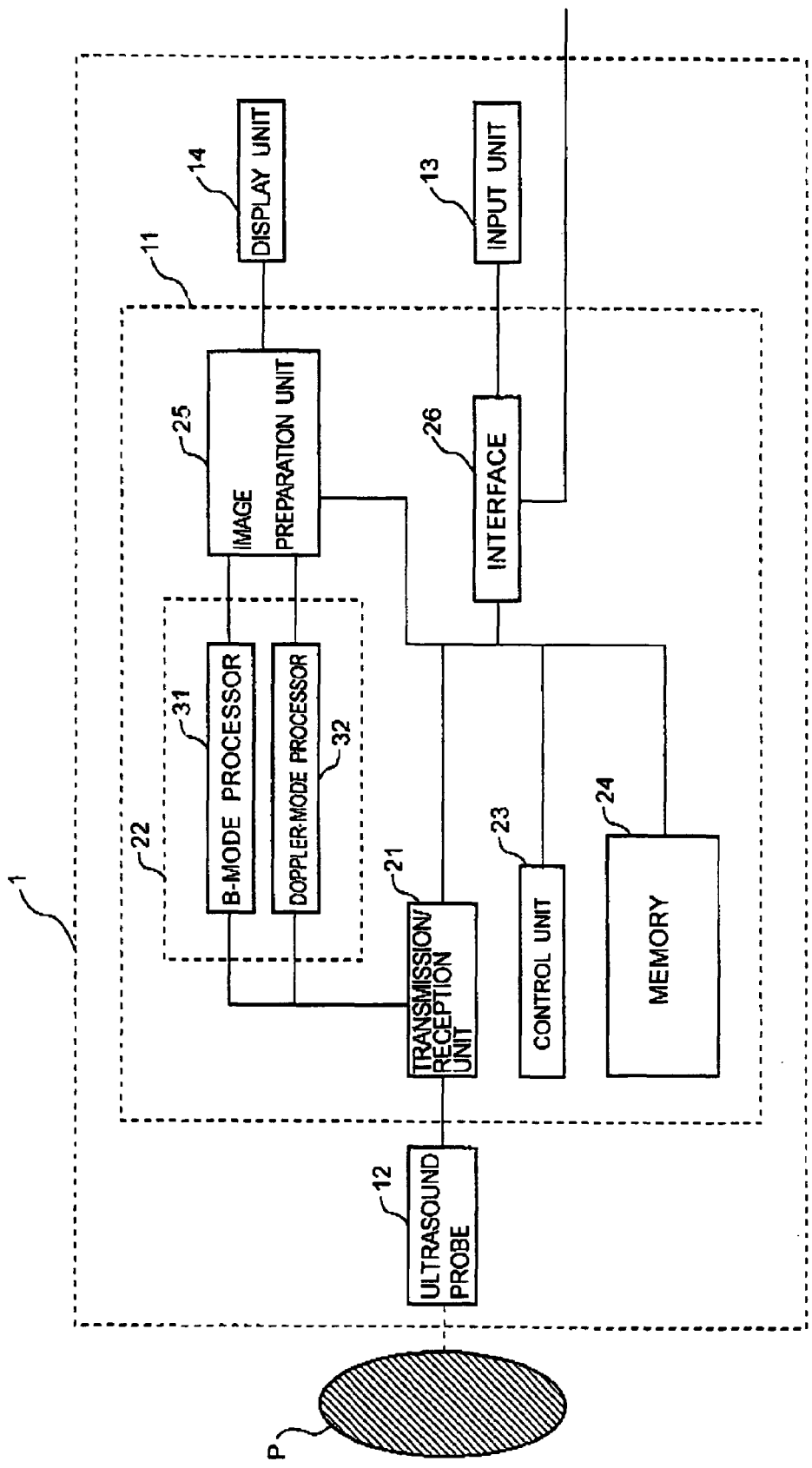
FIG. 1 is a block diagram showing an exemplary configuration of an ultrasound diagnosis apparatus.

FIG. 1 is a block diagram showing an exemplary configuration of an ultrasound diagnosis apparatus. An ultrasound diagnosis apparatus 1 may include a main unit 11, an ultrasound probe 12, an input unit 13, and a display unit 14.

The ultrasound probe 12 transmits ultrasound signals (or pulses) to a part of a patient P and receives echo signals resulting from the ultrasound transmission. The ultrasound probe 12 includes a plurality of arrayed piezoelectric transducers as acoustic-electric reversible conversion elements. The piezoelectric transducers receive voltage pulses supplied from the main unit 11 and accordingly oscillate so as to generate ultrasound pulses as the ultrasound signals. When the ultrasound probe 12 is contacted to a body surface of the patient P, the ultrasound signals pass into the inside of the patient P and reflect at surfaces where acoustic impedances differ. The reflected signals return to the ultrasound probe 12 as the echo signals. The echo signals are received by the piezoelectric transducers and converted to electric signals. Amplitude of the echo signals may depend on the difference of the acoustic impedances at the surfaces. In addition, when the ultrasound signals reflect at a moving object, for example, a blood flow or a cardiac wall, the echo signals may be subject to a frequency shift depending on a direction component of the moving object's velocity corresponding to a direction of the ultrasound signals (or ultrasound beams) according to a Doppler-effect.

The input unit 13 may include buttons, switches, a keyboard, a mouse, a trackball, a joystick, and/or a touch command screen. The input unit 13 may include an injection timer switch in any above form. The input unit 13 may be used to input various instructions. Accordingly, a user of the ultrasound diagnosis apparatus 1 such as, for example, a doctor can input information of imaging conditions as the instructions, with respect to ultrasound imaging, such as, for example, a gain dynamic range, a transmission frequency, a transmission focus position, a pulse repetition frequency (PRF), depth of a field of view, and/or a scan density flow velocity range. Also, the input unit 13 may also be used to input information of image name, patient information such as, for example, a patient name and a patient identification number (ID), and/or the like.

The display unit 14 may include a cathode ray tube (CRT) display or a crystal liquid display (LCD) and usually displays ultrasound image data (or ultrasound images). The ultrasound images may be still images or moving images with respect to the part of the patient P based on signals provided from the main unit 11. Hereinafter, 'image data' means moving image(s) unless otherwise stated.

The main unit 11 may include a transmission and reception unit 21, an echo signal processor 22, a control unit 23, a memory 24, an image preparation unit 25, and an interface 26.

The transmission and reception unit 21 supplies the ultrasound probe 12 with predetermined high frequency voltage pulses centered about f0 Hertz. The transmission and reception unit 21 also receives and amplifies the echo signals from the ultrasound probe 12, and further conducts predetermined processing on the received echo signals.

The echo signal processor 22 may include a B-mode processor 31 and a Doppler-mode processor 32. In the echo signal processor 22, the echo signals processed by the transmission and reception unit 21 are supplied to the B-mode processor 31 when the echo signals pertain to a B-mode. The echo signals processed by the transmission and reception unit 21 are supplied to the Doppler-mode processor 32 when the echo signals pertain to a Doppler-mode. The B-mode processor 31 processes the echo signals so as to produce B-mode image data. The Doppler-mode processor 32 processes the echo signals so as to produce Doppler-mode image data.

The control unit 23 controls over the ultrasound diagnosis apparatus 1 and may include an injection timer. Particularly, the control unit 23 receives the instructions from the input unit 13 and controls the image display in the display unit 14.

The memory 24 may store control programs which are necessary to acquire, process, and/or display the image data, and also store the image data. The image data may be stored in association with their image names (or file names), patient information such as, for example, a patient name and a patient ID, and information of time instant when the imaging has been conducted. The image data may also be stored in association with various imaging conditions at the time when the ultrasound imaging has been conducted. The imaging conditions may include a gain dynamic range, a transmission frequency, a transmission focus position, a pulse repetition frequency (PRF), depth of a field of view, and/or a scan density flow velocity range.

The image preparation unit 25 prepares B-mode image data or Doppler-mode image data based on the signals processed in the echo signal processor 22.

The interface 26 connects the input unit 13 to the control unit 23 and other units in the main unit 11 according to the necessity. The interface 26 may also connect the ultrasound diagnosis apparatus 1 to other devices.

In FIG. 1, the ultrasound probe 12 and the transmission and reception unit 21 may correspond to 'a transceiver'. The echo signal processor 22 and the image preparation unit 25 may correspond to 'a processor' and may also correspond to 'a second processor'. The control unit 23 may correspond to 'a control unit'. The memory 24 may correspond to 'a memory'. The interface 26 may correspond to 'an interface'. The input unit 13 may correspond to 'an input unit'. The display unit 13 may correspond to 'a display unit'.

Figure 2:
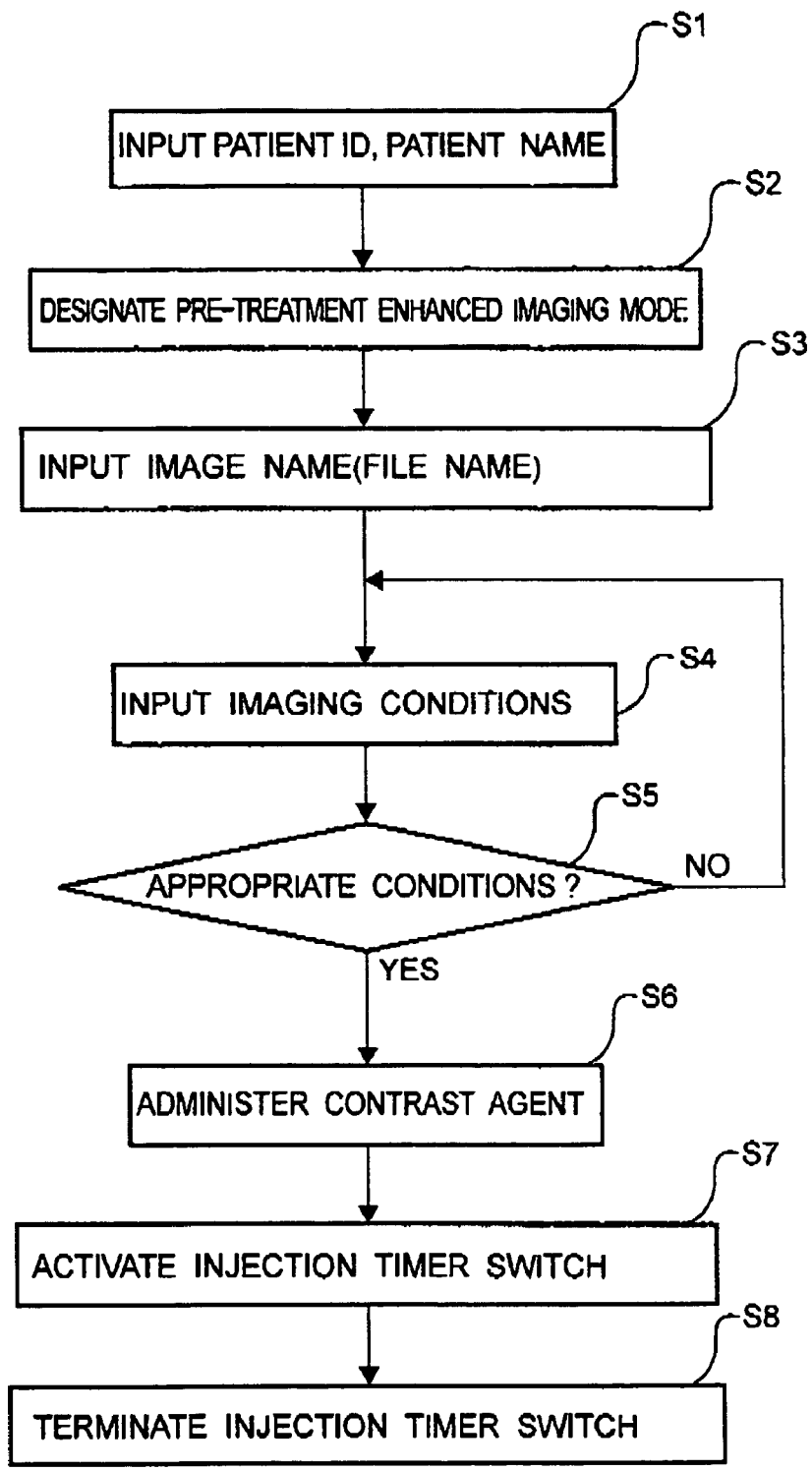
FIG. 2 is a flowchart showing an exemplary user operation in enhanced ultrasound imaging before a medical treatment.

FIG. 2 is a flowchart showing an exemplary user operation in enhanced ultrasound imaging before the medical treatment.

Figure 3:
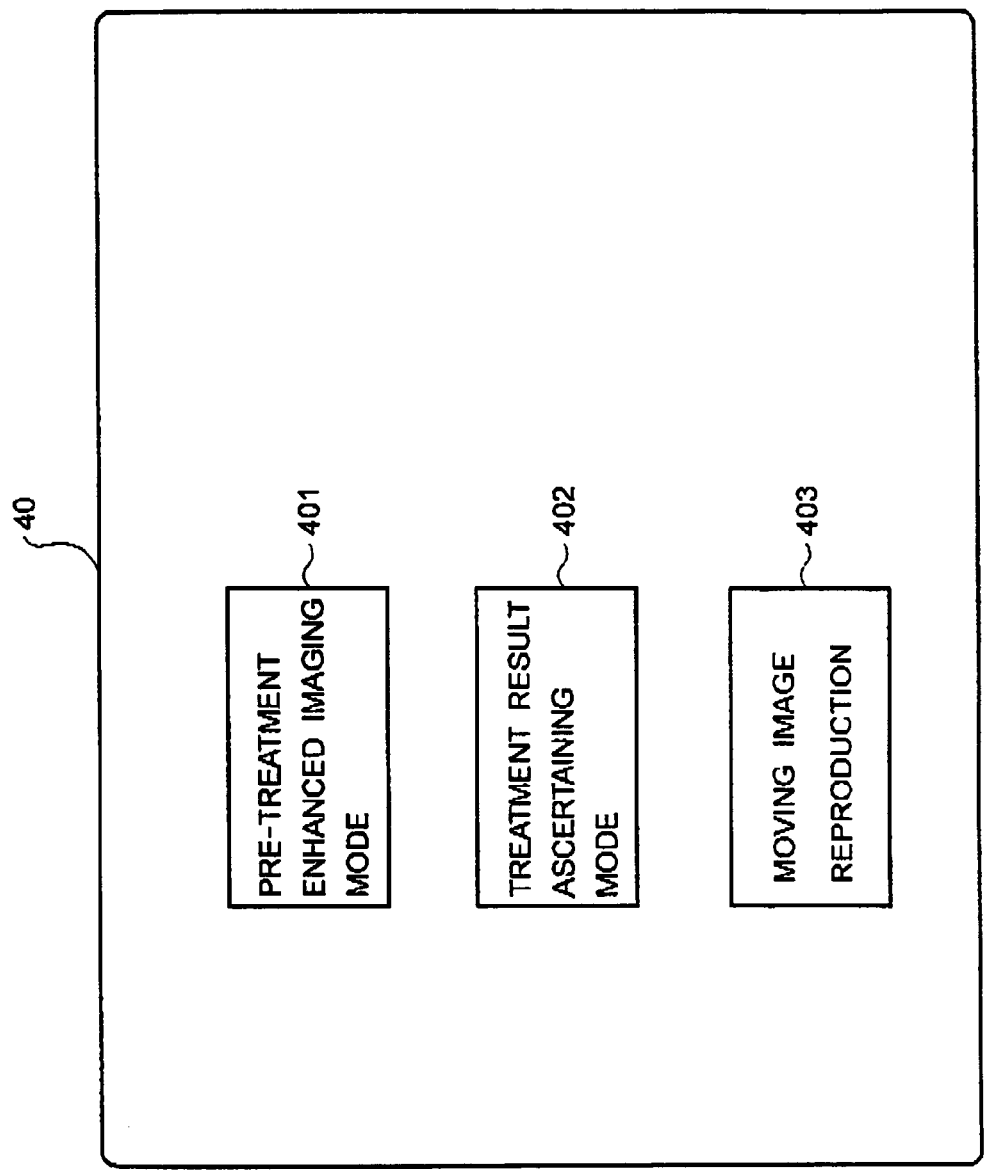
FIG. 3 is an illustration showing an example of a touch command screen for designating an operation mode of the ultrasound diagnosis apparatus.

As shown in FIG. 2, the user may first operate the input unit 13 so as to input, for example, a patient ID and a name of the patient P who is going to be imaged by the ultrasound diagnosis apparatus 1 (step S1). When the input unit 13 includes a touch command screen 40 shown in FIG. 3, the user touches a key 401 and designates a pre-treatment enhanced imaging mode (step S2). In response to the designation, the ultrasound diagnosis apparatus 1 (or the display unit 14) urges the user to input an image name (or a file name) to use when image data which will be acquired in the following operation are stored in the memory 24. The user operates the input unit 13 and inputs an image name 'INJ-1', for example (step S3).

The user then inputs imaging conditions such as, for example, a gain dynamic range, a transmission frequency, a transmission focus position, a pulse repetition frequency (PRF), depth of a field of view, and a scan density flow velocity range (step S4). The user may directly input detailed information of the above or alternatively select one of predetermined conditions with respect to each imaging condition. The operator may conduct image screening by contacting the ultrasound probe 12 onto the body surface of the patient P while ultrasound image data are displayed in the display unit 14 based on the above input or selected conditions. During the screening, the user checks the displayed image data and determines whether the contacting position of the ultrasound probe 12 is appropriate or not, whether imaging conditions of the displayed image data are appropriate or not, and the like (step S5). If the user has determined that the imaging conditions are not appropriate, the user may input alternate imaging conditions again in step S4.

When the user has determined that the imaging conditions are appropriate, the user initiates administration (or injection) of a contrast agent into the patient P (step S6). Almost at the same time as the administration, the user or a supporting staff of the user activates the injection timer switch by, for example, turning on, pressing on, selecting, inputting, or clicking on the injection timer switch (step S7).

In response to activation of the injection timer switch, the control unit 23 controls the transmission and reception unit 21 so that the ultrasound probe 12 transmits ultrasound signals towards the inside of the patient body. The ultrasound signals pass inside the patient body and return as the echo signals. The echo signals are received and converted to electric signals by the ultrasound probe 12 and processed by the echo signal processor 22 through the transmission and reception unit 21. Based on the processed signals, the image preparation unit 25 prepares image data. The image data are displayed in the display unit 14. The image data may be ultrasound image data enhanced with the contrast agent. Although it depends on the imaging conditions, the image data are typically displayed substantially in real time. Substantial real time display may mean that time taken from the ultrasound signal transmission to the display may be short enough for the user to feel that the image data are displayed in real time. Therefore, the user can observe the enhancement progress by the contrast agent in continuously displayed image data.

The injection timer initiates to measure an elapsed time from the activation of the injection timer switch. Since the injection timer is activated almost at the same time as the administration of the contrast agent in step S7, the elapsed time can substantially mean the time elapsed from the initiation of the administration. In other words, the activation of the injection timer switch can be construed as the administration initiation of the contrast agent.

Figure 4:
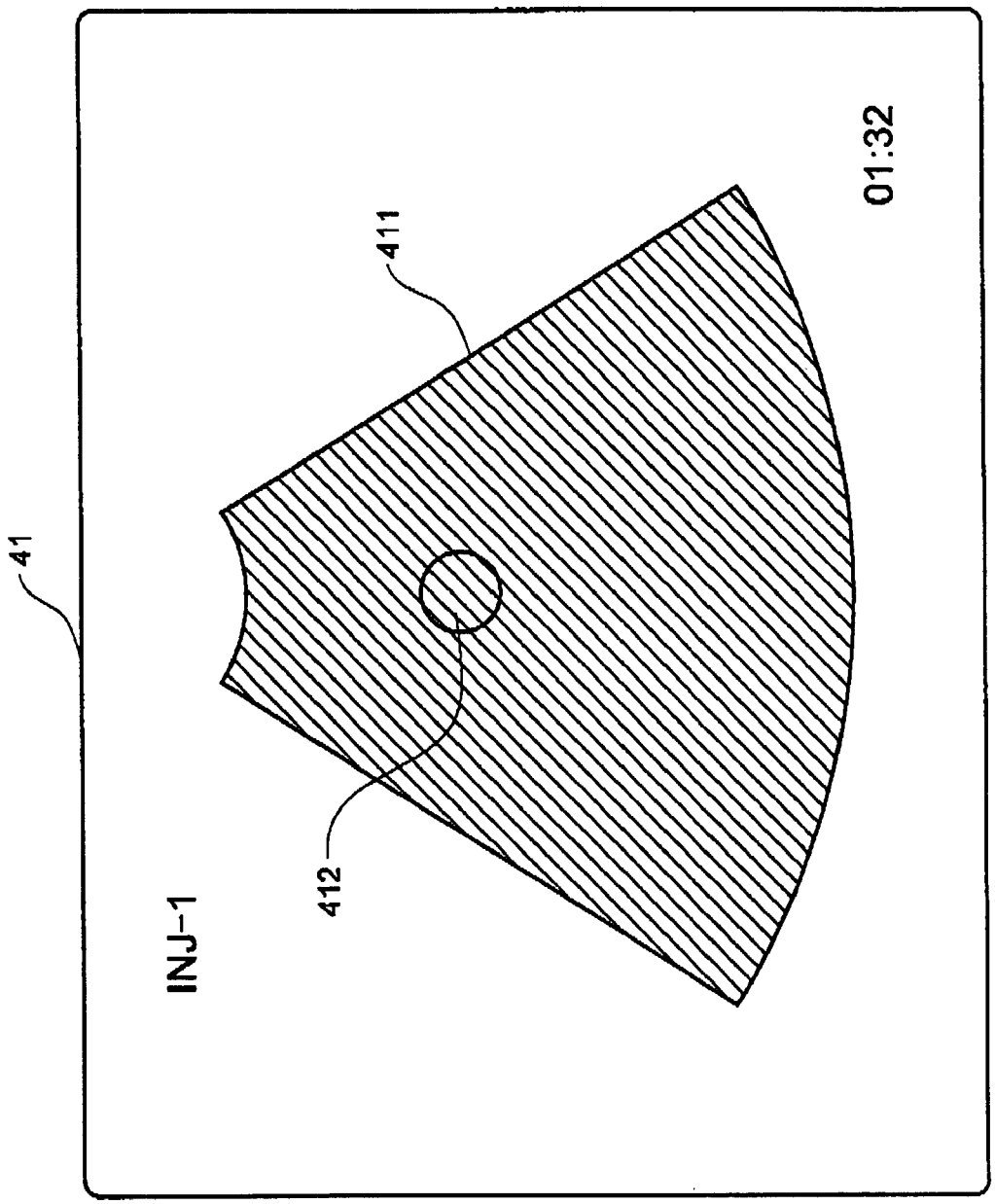
FIG. 4 is an illustration showing an example of image data display.

FIG. 4 is an illustration showing an example of the image data display. As shown in FIG. 4, the image name input in step S3 may be displayed at the upper left of a display window 41. The elapsed time (e.g., one minute thirty-two seconds) measured by the injection timer may be displayed at the lower right of the display window 41. The display window 41 shows an image 411 of the image data at a moment of a time phase (an elapsed time), one minute thirty-two seconds. In the image 411, the hatched part represents an enhanced part. After a certain period long enough for the contrast agent to flow into blood capillaries and tissues inside the liver, a whole part of the image data are enhanced and displayed as perfusion image data. In FIG. 4, a circle 412 represents a part of the tumor. Since the tumor is not medically treated yet and the contrast agent flows into the tumor through the blood vessels and the blood capillaries, the part of the tumor in the circle 412 is also hatched in FIG. 4.

The image data acquired according to the ultrasound signal transmission are also stored in the memory 24 as image data named 'INJ-1'. In addition, information of the time instant when the injection timer switch has been activated and of the elapsed time and imaging conditions input in step S4 may also be stored in association with the image data.

After the completion of the above imaging operations, the user may terminate the injection timer switch (step S8). In response to the termination, the storage of the image data and the elapsed time information is also terminated. The pre-treatment enhanced imaging mode is released.

If it is necessary to conduct similar enhanced imaging on the same patient P, steps S2 to S8 may be repeated.

As described above, the image data and associated information including the time instant, the elapsed time, and the imaging conditions are automatically stored in the memory 24 in response to the activation of the injection timer switch in the pre-treatment enhanced imaging mode. Therefore, it is advantageous for the user of needing no cumbersome or prompt operations which were usually required around the time of administration of the contrast agent.

After the above imaging, the user may conduct, for example, a focal medical treatment of the hepatocellular carcinoma such as the percutaneous ethanol injection therapy (PEIT), the percutaneous microwave coagulation therapy (PMCT), or the radiofrequency abration (RFA) on the patient P on the same day as or in one or more days after the above imaging.

After the medical treatment, the user may ascertain whether the medical treatment has successfully been conducted or not on the same day as or in one or more days after the medical treatment.

Figure 5:
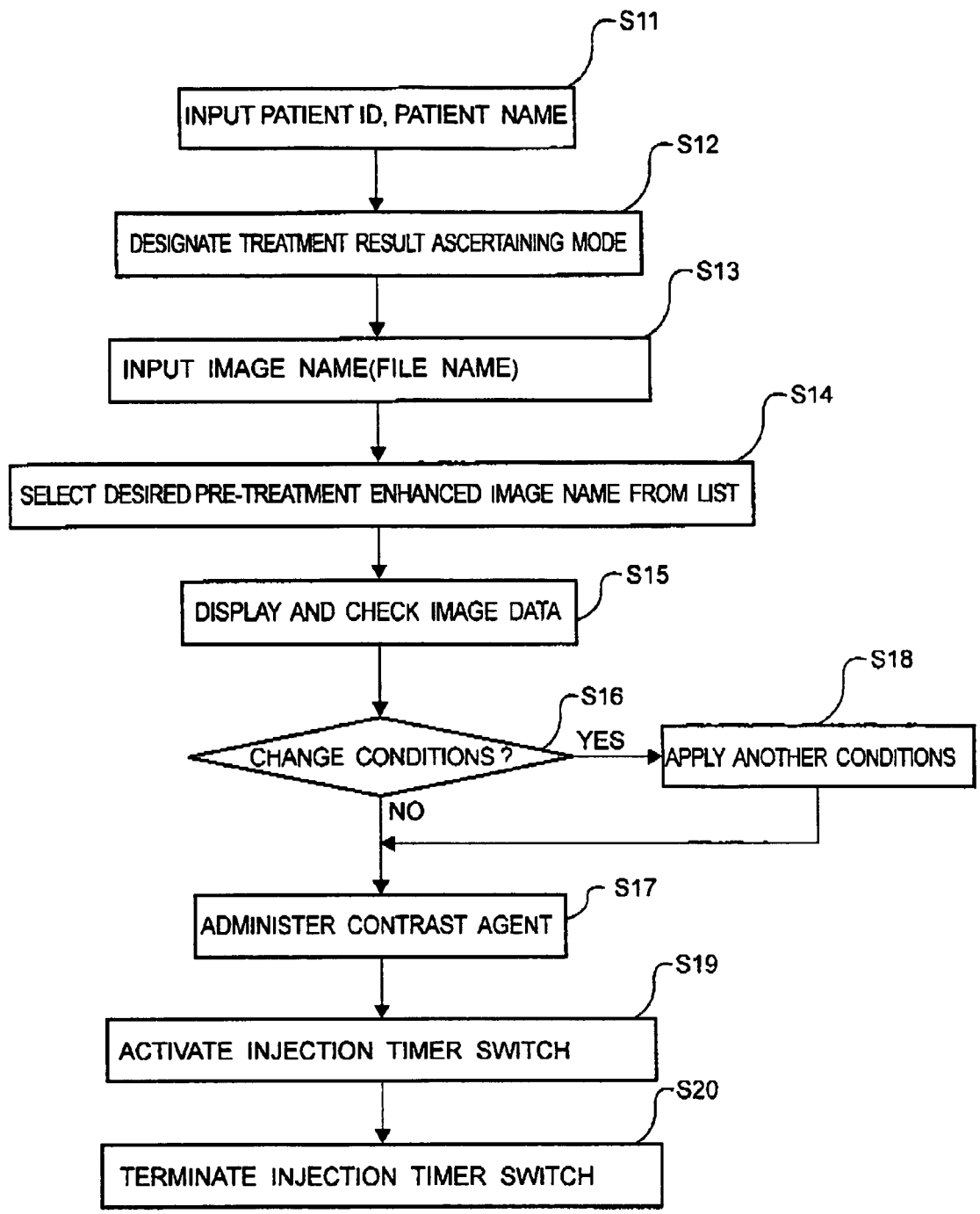
FIG. 5 is a flowchart showing an exemplary user operation in enhanced ultrasound imaging after the medical treatment.

FIG. 5 is a flowchart showing an exemplary user operation in enhanced ultrasound imaging after the medical treatment.

As shown in FIG. 5, the user may first operate the input unit 13 so as to input, for example, the patient ID and the name of the patient P who is going to be imaged by the ultrasound diagnosis apparatus 1 (step S11). The user touches a key 402 shown in FIG. 3 and designates a treatment result ascertaining mode (step S12). In response to the designation, the ultrasound diagnosis apparatus 1 (or the display unit 14) urges the user to input an image name (or a file name) to use when image data which will be acquired in the following operations are stored in the memory 24. The user operates the input unit 13 and inputs an image name 'INJ-AFTER-1', for example (step S13).

In response to the input of the image name, a list 42 of image names of pre-treatment image data with respect to the patient P corresponding to the patient ID and the patient name input in step 11 is shown in the display unit 14 as shown in FIG. 6. The pre-treatment image data are image data acquired before the medical treatment and may correspond to 'a past moving image data'. In the list 42, the patient ID and the patient name are displayed on the top, for example. Also in the list 42, image names of the pre-treatment image data are listed with their imaging date and time. This time may be the time instant when the injection timer switch has been activated. The user selects desired one of the listed image names (step S14). Although the user may typically select the latest one from the list according to the imaging date and time, the image name 'INJ-1' may be selected here, for example.

In response to the user's selection of the image name, the image data named 'INJ-1' stored in the memory 24 are displayed in the display unit 14. The image data named 'INJ-1' maybe displayed, for example, in the left side window of the display unit 14. The image data named 'INJ-1' may be repeatedly reproduced in response to the user's touching a key 403 shown in FIG. 3. After each reproduction, the image data named 'INJ-1' may be displayed by a still image corresponding to its initial frame of the moving image. If the user contacts the ultrasound probe 12 on the patient body, current ultrasound image data may be displayed, for example, in the right side window of the display unit 14. The user checks the displayed image data named 'INJ-1' (step S15) and determines whether it is fine to display post-treatment image data under the same imaging conditions as the imaged at a named 'INJ-1' or it is better to change imaging conditions (or to apply another imaging conditions) to the post-treatment image data which are going to be acquired in the following operations (step S16). The post-treatment image data are image data acquired after the medical treatment and may correspond to 'a current moving image data'. Typically, the same imaging conditions may be applied so that the pre-treatment and post-treatment image data can be compared under the same conditions. If, however, the user prefers not to apply the imaging conditions applied to the image data named 'INJ-1' to the post-treatment image data, the user may change imaging conditions for the post-treatment image data (step S18).

The user then initiates administration (or injection) of a contrast agent into the patient P (step S17). Almost at the same time as the administration, the user or the supporting staff of the user activates the injection timer switch by, for example, turning on, pressing on, selecting, inputting, or clicking on the injection timer switch (step S19).

In response to activation of the injection timer switch, the control unit 23 controls the transmission and reception unit 21 so that the ultrasound probe 12 transmits ultrasound signals towards the inside of the patient body. The ultrasound signals pass inside the patient body and return as the echo signals. The echo signals are received and converted to electric signals by the ultrasound probe 12 and processed by the echo signal processor 22 through the transmission and reception unit 21. Based on the processed signals, the image preparation unit 25 prepares post-treatment image data. The post-treatment image data are displayed in the right side window of the display unit 14. The post-treatment image data may be ultrasound image data enhanced with the contrast agent. Although it depends on the imaging conditions, the image data are typically displayed substantially in real time.

In the display unit 14, the image data named 'INJ-1' is also reproduced and displayed in the left side window of the display unit 14 in response to the activation of the injection timer switch in step S19. Therefore, the image data named 'INJ-1', that is, the pre-treatment image data may be displayed substantially in synchronization with the post-treatment image data in a sense that the elapsed time from the activation of the injection timer switch is synchronized although time elapsed from the administration for the pre-treatment image data may be slightly different from one for the post-treatment image data. Therefore, the user can observe the enhancement progress by the contrast agent in continuously displayed post-treatment image data, comparing to the enhancement progress in pre-treatment image data being displayed as the moving image. If the display unit 14 is not capable of displaying the pre-treatment and post-treatment image data in parallel as a single display unit, the pre-treatment image data may be displayed in another display unit connected to the main unit 11 as part of the display unit 14.

For the post-treatment image data, the injection timer also initiates to measure an elapsed time from the activation of the injection timer switch. Since the injection timer is activated almost at the same time as the administration of the contrast agent in step S19, the elapsed time can substantially mean the time elapsed from the initiation of the administration.

Figure 7:
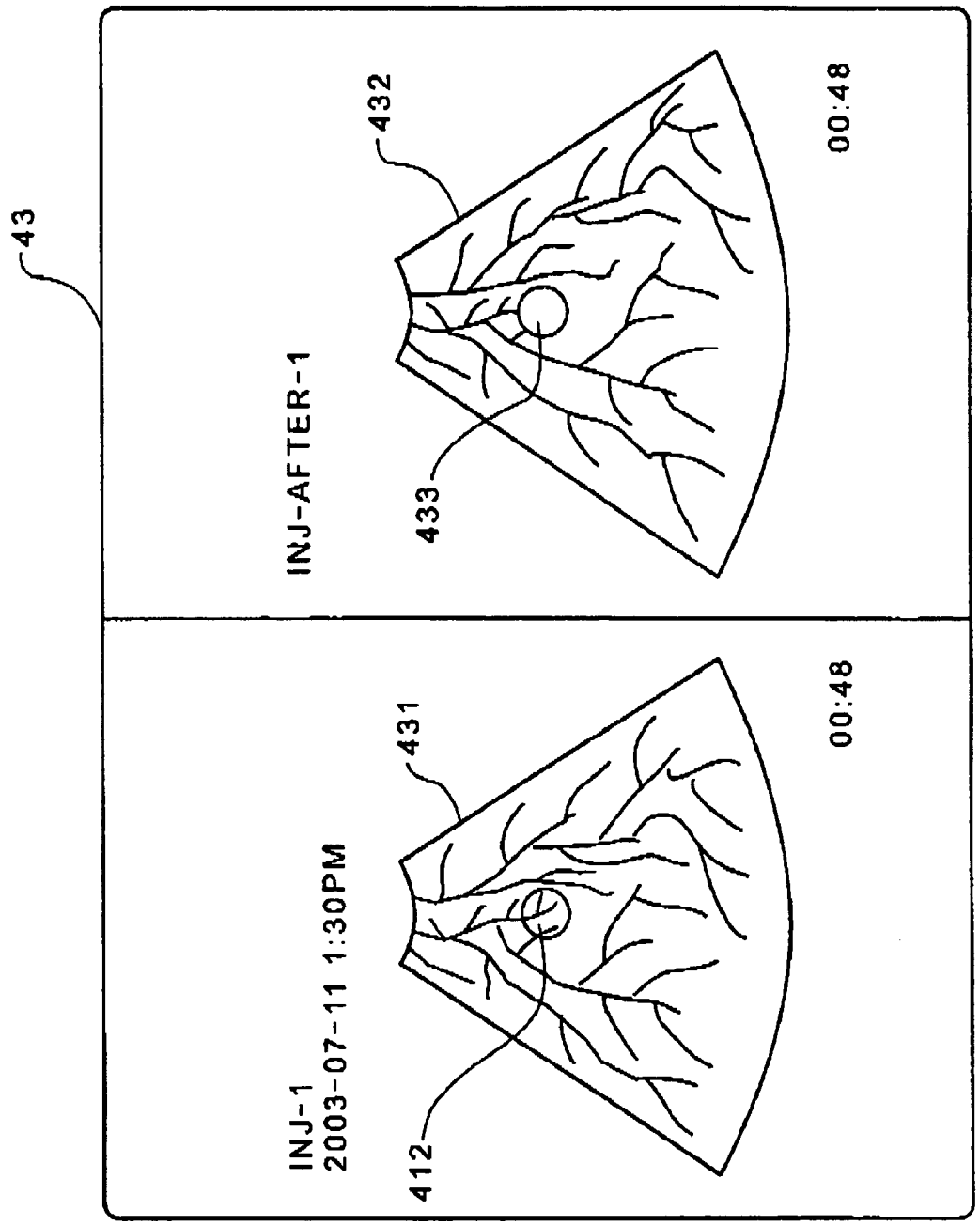
FIG. 7 is an illustration showing an example of comparison in a vascular image display.

FIG. 7 is an illustration showing an example of comparison in a vascular image display. As shown in FIG. 7, vascular images of the image data named 'INJ-1' and 'INJ-AFTER-1' are displayed in a display window 43 of the display unit 14 at an early stage of the enhancement progress after the administration of the contrast agent. In other words, the display window 43 shows an image 431 of the pre-treatment image data at a moment of a time phase (or an elapsed time), forty-eight seconds and an image 432 of the post-treatment image data at a moment of a time phase (or an elapsed time), forty-eight seconds. The image names input in steps S3 and S13 may be displayed for the images 431 and 432, respectively. For the image 431, the date and the time instant of the imaging may also be displayed with the image name 'INJ-1' The elapsed time (e.g., forty-eight seconds) measured by the injection timer may be displayed for both the images 431 and 432. The displayed images 431 and 432 are synchronized with respect to the elapsed time from each activation of the injection timer switch.

Since the images 431 and 432 are vascular images, only blood vessels are enhanced in the images 431 and 432. Each of circles 412 and 433 represents a part of the tumor. Since the image 431 shows that the tumor is not medically treated and the contrast agent flows into the tumor through the blood vessels, the enhanced blood vessels are observed in the circle 412. On the other hand, since the image 432 shows that the tumor has already been medically treated and the contrast agent is prevented from flowing into the tumor through the blood vessels, the enhanced blood vessels are not observed in the circle 433.

Figure 8:
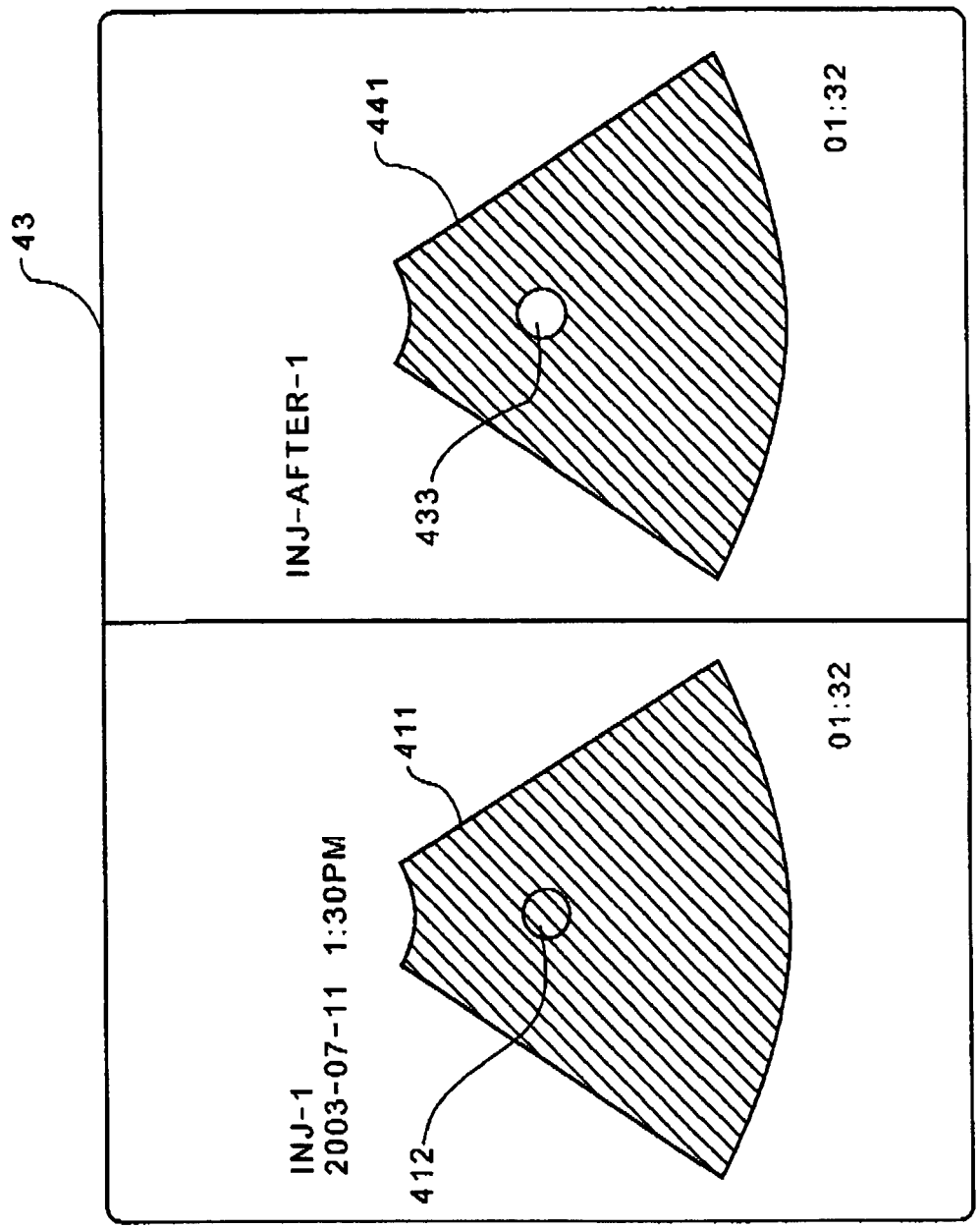
FIG. 8 is an illustration showing an example of comparison in a perfusion image display.

FIG. 8 is an illustration showing an example of comparison in a perfusion image display. As shown in FIG. 8, perfusion images of the image data named 'INJ-1' and 'INJ-AFTER-1' are displayed in a display window 44 of the display unit 14 at an later stage of the enhancement progress after the administration of the contrast agent. In other words, the display window 44 shows the image 411 of the pre-treatment image data at a moment of a time phase (or an elapsed time), one minute thirty-two seconds and an image 441 of the post-treatment image data at a moment of a time phase (or an elapsed time) one minute thirty-two seconds. Similar to the display window 43, the image names input in steps S3 and S13 maybe displayed for the images 411 and 441, respectively. For the image 411, the date and the time instant of the imaging may also be displayed with the image name 'INJ-1' The elapsed time (e.g., one minute thirty-two seconds) measured by the injection timer may be displayed for both the images 411 and 441. The displayed images 411 and 441 are synchronized with respect to the elapsed time from each activation of the injection timer switch.

Since the images 411 and 441 are perfusion images, hatched part represents an enhanced part. After a certain period long enough for the contrast agent to flow into blood capillaries and tissues inside the liver, a whole part of the image data are enhanced and displayed as perfusion image data. Since the image 411 shows that the tumor is not medically treated and the contrast agent flows into the tumor through the blood vessels and the blood capillaries, the part of the tumor in the circle 412 is also hatched. On the other hand, the circle 433 is not hatched since the image 441 shows that the tumor has already been medically treated and the contrast agent is prevented from flowing into the tumor through the blood vessels and the blood capillaries as a result of the medical treatment. In other words, the user can ascertain that the medical treatment has successfully been conducted by observing that the enhanced blood vessels, blood capillaries, and tissues are not appearing in the circle 433.

The post-treatment image data acquired according to the ultrasound signal transmission are also stored in the memory 24 as image data named 'INJ-AFTER-1'. In addition, information of the time instant when the injection timer switch has been activated and of the elapsed time and imaging conditions may also be stored in association with the post-treatment image data.

After the completion of the above imaging operations, the user may terminate the injection timer switch (step S20). In response to the termination, the storage of the image data and the elapsed time information is also terminated. The treatment result ascertaining mode is released.

If it is necessary to conduct similar enhanced imaging on the same patient P, steps S12 to S20 may be repeated.

If the user can observe that the enhanced blood vessels, blood capillaries, and tissues are still appearing in the circle 433, the user may determine that the medical treatment has not completely succeeded and conduct another medical treatment on the patient P. The image name 'INJ-AFTER-1' may be added to the list 42 shown in FIG. 6 and can be selected as an image name with respect to the latest pre-treatment image data in the selection in step S14 when the user conducts the next operations in the treatment result ascertaining mode.

As described above, the user only needs to (administer the contrast agent and) activate the injection timer switch so as to observe the post-treatment image data by comparing to the pre-treatment image data in a synchronizing manner. For example, the vascular image data, the perfusion image data, or image data at any time phase can be easily and accurately compared between the pre-treatment image data and the post-treatment image data in a synchronizing manner.

Figure 9:
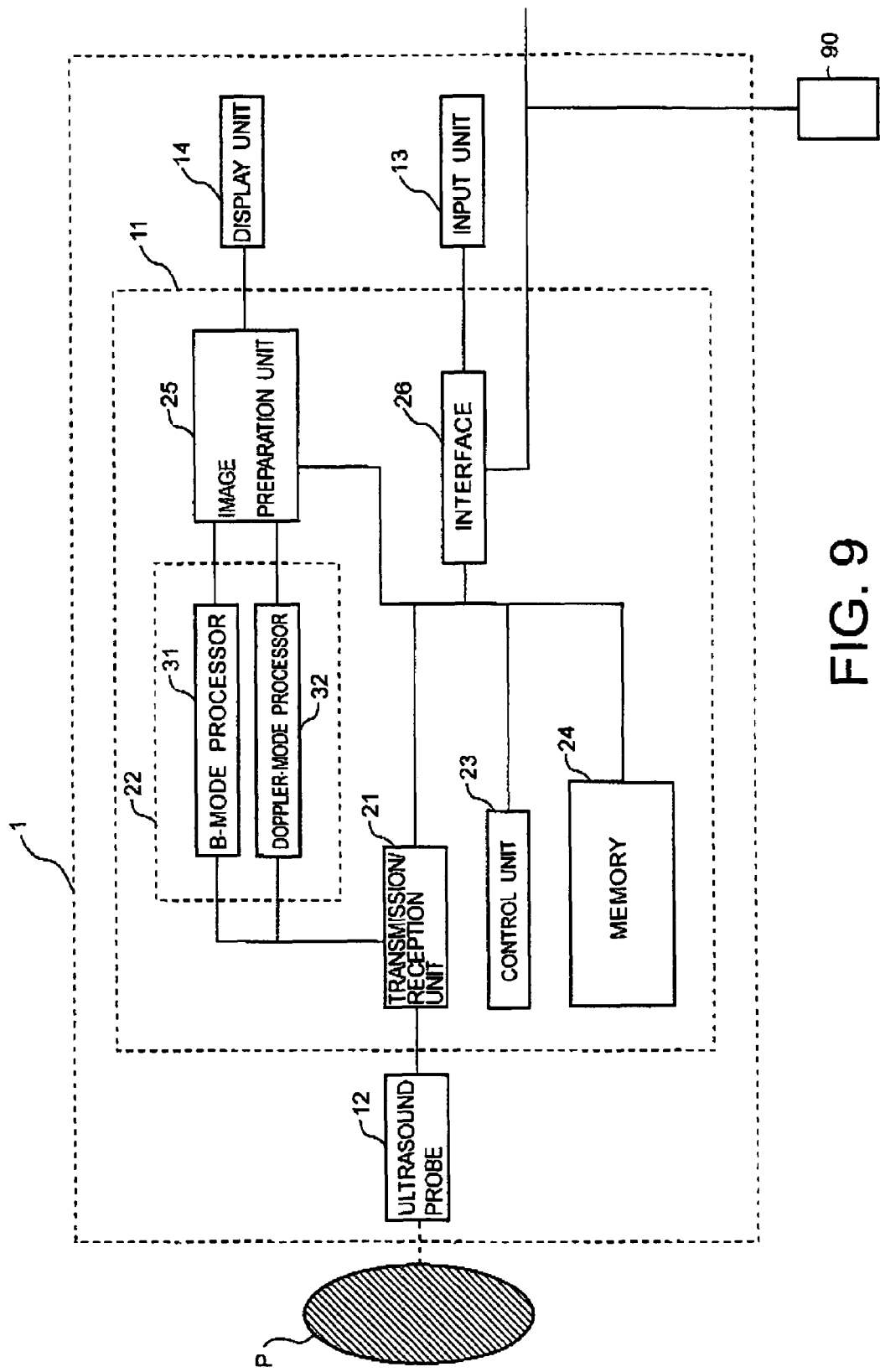
FIG. 9 is a block diagram showing a modification of the ultrasound diagnosis apparatus shown in FIG. 1.

The following modifications may also be made with respect to the embodiments of the ultrasound diagnosis apparatus. FIG. 9 is a block diagram showing a modification of the ultrasound diagnosis apparatus shown in FIG. 1. As shown in FIG. 9, the ultrasound diagnosis apparatus 1 may electrically be connected to an external injector 90 through the interface 26. The external injector may be provided independent of the ultrasound diagnosis apparatus 1. When the user activates the injection timer switch in the input unit 13, the control unit 23 activates the injection timer in response to the reception of the activation instruction. In addition, an activation control signal is provided from the control unit 23 to the external injector 90 through the interface 26 in response to the reception of the activation instruction. The external injector 90 may be activated to administer the contrast agent if the external injector 90 is provided to be ready for the administration into the patient body with its needle.

Alternatively, the user may activate the external injector 90 by operating the external injector 90. The external injector 90 may initiate to administer the contrast agent in response to the activation operation. The external injector 90 may also provide an activation instruction to the control unit 23 through the interface 26 in response to the activation operation. The control unit 23 may activate the injection timer in response to the reception of the activation instruction from the external injector 90.

In the above modifications, the administration of the contrast agent and the activation of the injection timer are automatically engaged with a single operation such as the activation of the injection timer switch in the input unit 13 or the activation of the external injector 90. In addition, the user may not need a support of the supporting staff. Therefore, it may be possible to improve the accuracy of the synchronization between the initiation of the administration and the initiation of the measurement in the injection timer. It can also reduce the user's operations.

The rest of the operations in the ultrasound diagnosis apparatus 1 may be similar to those shown in FIG. 1.

As another modification of the embodiments, the image preparation unit 25 may conduct image processing on the pre-treatment image data in advance so as to determine luminance level by the contrast agent in the pre-treatment image data and a time phase when the luminance level determined on a predetermined part (e.g. a region of interest such as the part of the tumor) has reached a predetermined reference level. The predetermined reference level and elapsed time corresponding to the time phase may be stored in the memory 24. When the post-treatment image data are being displayed, the image preparation unit 25 may also conduct image processing on the post-treatment image data so as to determine whether luminance level by the contrast agent on a part corresponding to the predetermined part has reached the predetermined reference level or not. When the image preparation unit 25 has determined that the luminance level has reached the predetermined reference level, the pre-treatment image data may be displayed from the stored time phase so that the pre-treatment image data and the post-treatment image data can be displayed in a synchronizing manner.

The above modification is only an example. Any types of image processing maybe applicable for achieving a synchronized display.

Still further modification of the embodiments may pertain to a display of one or more still images. Although moving images are displayed as the pre-treatment and post-treatment image data in the embodiments described above, one or more still images may be displayed as the pre-treatment image data. For example, one or more still images at specific time phases may be prepared originally in the pre-treatment enhancement imaging or prepared by extracting one or more frames from the moving pre-treatment image data as such still images. The prepared still images may be stored in association with elapsed time (or time phase) information in the memory 24. The stored still images may be displayed at corresponding time phases of the post-treatment image data during the display of the post-treatment image data as a moving image. Once one still image has been displayed, the one still image may be displayed for a while. For example, such one still image may be displayed for a predetermined period or continue to be displayed until the next one still image is displayed.

The embodiments of the present invention described above are examples described only for making it easier to understand the present invention, and are not described for the limitation of the present invention. Consequently, each component and element disclosed in the embodiments of the present invention may be redesigned or modified to its equivalent within a scope of the present invention. Furthermore, any possible combination of such components and elements may be included in a scope of the present invention as long as an advantage similar to those obtained according to the above disclosure in the embodiments of the present invention is obtained.

Numerous modifications and variations of the present invention are possible in light of the above teachings. It is therefore to be understood that within the scope of the appended claims, the invention may be practiced otherwise than as specifically described herein.

The invention claimed is:

1. An ultrasound diagnosis apparatus, comprising:
a transceiver configured to transmit an ultrasound signal to a part of a specimen having been subjected to an administration of a contrast agent and to receive an echo signal resulting from the ultrasound signal transmission;
a processor configured to prepare moving image data based on the received echo signal;
a memory that stores the prepared moving image data of a pre-treatment for an object after a first administration of the contrast agent as past moving image data; and
a display unit display that displays, at a same time, the past moving image data of the pre-treatment and current moving image data of a post-treatment for the object being prepared by the processor, the processor causing the past moving image data to be displayed in response to a start of a second administration of the contrast agent corresponding to the current moving image data.

2. The apparatus according to claim 1, wherein the memory is further configured to store a first imaging condition in association with the past moving image data.

3. The apparatus according to claim 2, further comprising a control unit configured to compare the first imaging condition to a second imaging condition associated with the current moving image data and to control the apparatus based on a result of the comparison.

4. The apparatus according to claim 1, further comprising an injection timer configured to measure an elapsed time from a start of administration of the contrast agent, wherein the memory is further configured to store information of the measured elapsed time in association with the past moving image data.

5. The apparatus according to claim 1, further comprising an injection timer configured to measure an elapsed time from a start of administration of the contrast agent, wherein, when the display unit displays the past moving image data and the current moving image data, the display unit displays the past moving image data substantially in synchronization with the current moving image data with respect to the elapsed time.

6. The apparatus according to claim 1, further comprising an input unit configured to input an instruction, wherein the memory is further configured to store time instant information in association with the past moving image data, and the display unit is further configured to display a list of the stored time instant information of the past moving image data and to display the past moving image data corresponding to the stored time instant information selected from the list by the instruction.

7. The apparatus according to claim 1, wherein the past moving image data is prepared based on the echo signal received before a medical treatment on the part of the specimen, and the current moving image data is prepared based on the echo signal received after the medical treatment.

8. The apparatus according to claim 1, wherein the part of the specimen includes a part of a liver.

9. The apparatus according to claim 1, further comprising:
an input unit configured to input an instruction of a start of administration of the contrast agent;
an injection timer configured to measure an elapsed time from the start of administration; and
a control unit configured to control the injection timer to initiate the measurement in response to the instruction.

10. The apparatus according to claim 9, wherein the control unit is further configured to provide the instruction to an external injector connected to the apparatus so that the injector initiates the administration.

11. The apparatus according to claim 1, further comprising:
an interface configured to connect the apparatus to an external injector and to receive an instruction of a start of administration of the contrast agent from the external injector;
an injection timer configured to measure an elapsed time from the start of administration; and
a control unit configured to control the injection timer to initiate the measurement in response to the received instruction.

12. The apparatus according to claim 1, further comprising a second processor configured to conduct an image processing on the moving image data, wherein start of administration of the contrast agent is determined based on the image processing.

13. An ultrasound diagnosis apparatus, comprising:
a transceiver configured to transmit an ultrasound signal to a part of a specimen having been subjected to an administration of a contrast agent and to receive an echo signal resulting from the ultrasound signal transmission;
a processor configured to prepare image data based on the received echo signal;
a memory that stores the image data for at least one image of a pre-treatment for an object after a first administration of the contrast agent as past image data; and
a display unit display that displays, at a same time, the past image data of the pre-treatment and current image data of a post-treatment for the object being prepared by the processor, the processor causing the past image data to be displayed in accordance with a time phase of the current image data based on a start of a second administration of the contrast agent corresponding to the current image data.

14. The apparatus according to claim 13, wherein the past image data is displayed as at least one still image.

15. The apparatus according to claim 13, wherein the image data includes moving image data, and the past image data is prepared based on the moving image data.

16. The apparatus according to claim 13, wherein the image data includes moving image data, and the current image data includes the moving image data.

17. The apparatus according to claim 13, wherein the memory is further configured to store a first imaging condition in association with the past image data.

18. The apparatus according to claim 17, further comprising a control unit configured to compare the first imaging condition to a second imaging condition associated with the current image data and to control the apparatus based on a result of the comparison.

19. The apparatus according to claim 13, further comprising an injection timer configured to measure an elapsed time from a start of administration of the contrast agent, wherein the memory is further configured to store information of the measured elapsed time in association with the past image data.

20. The apparatus according to claim 13, further comprising an injection timer configured to measure an elapsed time from a start of administration of the contrast agent, wherein, when the display unit displays the past image data and the current image data, the display unit displays the past image data substantially in synchronization with the current image data with respect to the elapsed time.

21. The apparatus according to claim 13, further comprising an input unit configured to input an instruction, wherein the memory is further configured to store time instant information in association with the past image data, and the display unit is further configured to display a list of the stored time instant information of the past image data and to display the past image data corresponding to the stored time instant information selected from the list by the instruction.

22. The apparatus according to claim 13, wherein the past image data is prepared based on the echo signal received before a medical treatment on the part of the specimen, and the current image data is prepared based on the echo signal received after the medical treatment.

23. The apparatus according to claim 13, wherein the part of the specimen includes a part of a liver.

24. The apparatus according to claim 13, further comprising:
an input unit configured to input an instruction of a start of administration of the contrast agent;
an injection timer configured to measure an elapsed time from the start of administration; and
a control unit configured to control the injection timer to initiate the measurement in response to the instruction.

25. The apparatus according to claim 24, wherein the control unit is further configured to provide the instruction to an external injector connected to the apparatus so that the injector initiates the administration.

26. The apparatus according to claim 13, further comprising:
an interface configured to connect the apparatus to an external injector and to receive an instruction of a start of administration of the contrast agent from the external injector;
an injection timer configured to measure an elapsed time from the start of administration; and
a control unit configured to control the injection timer to initiate the measurement in response to the received instruction.

27. The apparatus according to claim 13, further comprising a second processor configured to conduct image processing on the image data, wherein the start of injection of the contrast agent is determined based on the image processing.

28. A method of displaying an ultrasound image resulting from an ultrasound diagnosis apparatus, the method comprising:
transmitting a first ultrasound signal to a part of a specimen having been subjected to a first administration of a contrast agent and receiving a first echo signal resulting from the first ultrasound signal transmission;
preparing first moving image data based on the received first echo signal;
storing the prepared first moving image data of a pre-treatment for an object as past moving image data;
transmitting a second ultrasound signal to the part having been subjected to a second administration of the contrast agent of the specimen and receiving a second echo signal resulting from the second ultrasound signal transmission;
preparing second moving image data of a post-treatment for the object based on the received second echo signal; and
displaying the past moving image data of the pre-treatment and the second moving image data at a same time, the past moving image data being displayed in response to a start of the second administration of the contrast agent corresponding to the current moving image data.

29. The method according to claim 28, further comprising storing a first imaging condition in association with the past moving image data.

30. The method according to claim 29, further comprising comparing the first imaging condition to a second imaging condition associated with the second moving image data and controlling the apparatus based on a result of the comparison.

31. The method according to claim 28, further comprising:
   measuring an elapsed time from a start of administration the contrast agent; and
   storing information of the measured elapsed time in association with the past moving image data.

32. The method according to claim 28, further comprising:
   measuring an elapsed time from a start of administration of the contrast agent; and
   displaying the past moving image data substantially in synchronization with the second moving image data with respect to the elapsed time when the past moving image data and the second moving image data are displayed.

33. The method according to claim 28, further comprising:
   inputting an instruction;
   storing time instant information in association with the past moving image data;
   displaying a list of the stored time instant information of the past moving image data; and
   displaying the past moving image data corresponding to the stored time instant information selected from the list by the instruction.

34. The method according to claim 28, wherein the past moving image data is prepared based on the echo signal received before a medical treatment on the part of the specimen, and the second moving image data is prepared based on the echo signal received after the medical treatment.

35. The method according to claim 28, wherein the part of the specimen includes a part of a liver.

36. The method according to claim 28, further comprising:
   inputting an instruction of a start of administration of the contrast agent;
   measuring an elapsed time from the start of administration; and
   controlling to initiate the measurement in response to the instruction.

37. The method according to claim 36, further comprising providing the instruction to an external injector connected to the apparatus so that the start of administration is initiated.

38. The method according to claim 28, further comprising:
   receiving an instruction of a start of administration of the contrast agent from an external injector connected to the apparatus;
   measuring an elapsed time from the start of administration; and
   controlling a start of the measurement in response to the received instruction.

39. The method according to claim 28, further comprising conducting image processing on the past and second moving image data, wherein a start of injection of the contrast agent is determined based on the image processing.

* * * * *